US011285266B2

(12) United States Patent
Fitzgibbon et al.

(10) Patent No.: US 11,285,266 B2
(45) Date of Patent: Mar. 29, 2022

(54) DRUG DELIVERY DEVICE HAVING MINIMIZED RISK OF COMPONENT FRACTURE UPON IMPACT EVENTS

(71) Applicant: AMGEN INC., Thousand Oaks, CA (US)

(72) Inventors: Sean Fitzgibbon, Camarillo, CA (US); Julian Jazayeri, Woodland Hills, CA (US)

(73) Assignee: AMGEN INC., Thousand Oaks, CA (US)

( * ) Notice: Subject to any disclaimer, the term of this patent is extended or adjusted under 35 U.S.C. 154(b) by 499 days.

(21) Appl. No.: 16/306,810

(22) PCT Filed: May 15, 2017

(86) PCT No.: PCT/US2017/032605
§ 371 (c)(1),
(2) Date: Dec. 3, 2018

(87) PCT Pub. No.: WO2018/004842
PCT Pub. Date: Jan. 4, 2018

(65) Prior Publication Data
US 2019/0167908 A1    Jun. 6, 2019

Related U.S. Application Data

(60) Provisional application No. 62/357,713, filed on Jul. 1, 2016.

(51) Int. Cl.
*A61M 5/315*    (2006.01)
*A61M 5/20*    (2006.01)
(Continued)

(52) U.S. Cl.
CPC ...... *A61M 5/31513* (2013.01); *A61M 5/1454* (2013.01); *A61M 5/2033* (2013.01);
(Continued)

(58) Field of Classification Search
CPC .......... A61M 5/31513; A61M 5/31515; A61M 5/20; A61M 5/2448; A61M 5/1454;
(Continued)

(56) References Cited

U.S. PATENT DOCUMENTS

2009/0163867 A1*  6/2009  Marshall ........... A61M 5/31586
                                                    604/136
2011/0178500 A1*  7/2011  Shang ..................... A61P 29/00
                                                    604/506
(Continued)

FOREIGN PATENT DOCUMENTS

WO    WO-2013119591 A1    8/2013

OTHER PUBLICATIONS

International Search Report and Written Opinion for International Application No. PCT/US2017/032605, dated Aug. 30, 2017.
(Continued)

*Primary Examiner* — Kevin C Sirmons
*Assistant Examiner* — Alexandra Lalonde
(74) *Attorney, Agent, or Firm* — Marshall, Gerstein & Borun LLP

(57) ABSTRACT

A drug delivery device includes a reservoir, a drug delivery member in fluid communication with the reservoir, and a plunger disposed in and moveable relative to the reservoir. A plunger rod has a mass $M_P$ and is movable from (i) a first position, where the distal end of the plunger rod is spaced apart from the plunger to (ii) a second position, where the distal end of the plunger rod contacts the plunger. A drive mechanism is coupled to the proximal end of the plunger rod and is configured to deliver a drive force $F_D$ to move the plunger rod from the first position to the second position. A ratio of the mass of the plunger rod to the drive force of the drive mechanism ($M_P/F_D$) is in a range of approximately a value greater than 0 kg/kgf to approximately 0.05 kg/kgf.

14 Claims, 6 Drawing Sheets

(51) Int. Cl.
*A61M 5/32* (2006.01)
*A61M 5/145* (2006.01)

(52) U.S. Cl.
CPC ........ *A61M 5/31511* (2013.01); *A61M 5/322* (2013.01); *A61M 2207/00* (2013.01)

(58) Field of Classification Search
CPC .... A61M 5/2033; A61M 5/322; A61M 5/284; A61M 5/31511; A61M 2005/2086; A61M 2005/287; A61M 5/315; A61M 5/28; A61M 5/286; A61M 5/178; A61M 5/24; A61M 5/2459; A61M 5/2466; A61M 5/288; A61M 2005/2462; A61M 2207/00
See application file for complete search history.

(56) References Cited

U.S. PATENT DOCUMENTS

| | | | |
|---|---|---|---|
| 2013/0289490 A1* | 10/2013 | Kemp | A61M 5/3287 604/198 |
| 2014/0012229 A1 | 1/2014 | Bokelman et al. | |
| 2014/0330216 A1 | 11/2014 | Weaver et al. | |

OTHER PUBLICATIONS

International Preliminary Report on Patentability and Written Opinion for International Application No. PCT/US2017/032605, dated Jan. 10, 2019.

\* cited by examiner

DRUG DELIVERY DEVICE HAVING MINIMIZED RISK OF COMPONENT FRACTURE UPON IMPACT EVENTS

CROSS-REFERENCE TO RELATED APPLICATIONS

This is the United States national phase of International Patent Application No. PCT/US2017/032605, filed May 15, 2017, which claims priority to U.S. Provisional Application No. 62/357,713, filed Jul. 1, 2016, the entire contents of each of which are hereby incorporated herein by reference.

FIELD OF THE DISCLOSURE

The present disclosure relates to a drug delivery device and a method of manufacturing a drug delivery device and, more particularly, to a spring-loaded drug delivery device and method of manufacturing a spring-loaded drug delivery device having minimal risk of component fracture from injection impact events.

BACKGROUND

Drug delivery devices, such as autoinjectors, on-body injectors, and hand-held injectors, are commonly prescribed for patients to self-administer medication. Such devices typically include a drive mechanism (e.g., a spring) that operates on a prefilled syringe in response to a triggering event, such as the patient pressing a button on the device. The drive mechanism creates a drive force and, additionally, operates on a plunger to deliver the medication subcutaneously via the needle. These drug delivery devices may be constructed as single-use or reusable devices.

Autoinjectors and on-body injectors offer several benefits in drug delivery over conventional syringes, such as simplicity of use. Autoinjectors and on-body injectors are beneficial for delivering drugs with high viscosities. However, as viscosity increases, the drive force required to inject the drug also increases. A large drive force may cause internal pressure build-up within the device, causing the prefilled syringe to fracture during injection.

SUMMARY

The present disclosure minimizes risk of component failure for drug delivery devices that sustain one or more impact events during injection. Specifically, the present disclosure addresses the impact forces imparted on a reservoir of a spring-loaded drug delivery device. In accordance with one or more aspects described herein, a drug delivery device and a method of manufacturing a drug delivery device may reduce peak internal pressure of a spring-loaded drug delivery device during injection without compromising the drug delivery.

In accordance with a first exemplary aspect, a drug delivery device may include a reservoir having a distal end and a proximal end, a drug delivery member in fluid communication with the distal end of the reservoir, a plunger disposed in and moveable relative to the reservoir, and a plunger rod having a mass $M_P$, a distal end and a proximal end. The plunger rod may be movable from (i) a first position, where the distal end of the plunger rod is spaced apart from the plunger to (ii) a second position, where the distal end of the plunger rod contacts the plunger. The drug delivery device may further include a drive mechanism that is coupled to the proximal end of the plunger rod and that is configured to deliver a drive force $F_D$ to move the plunger rod from the first position to the second position. A ratio of the mass of the plunger rod to the drive force of the drive mechanism ($M_P/F_D$) may be in a range of approximately a value greater than 0 kg/kgf to approximately 0.05 kg/kgf. In other embodiments, the ratio of the mass of the plunger rod to the drive force of the drive mechanism may be expanded beyond this range.

In accordance with a second exemplary aspect, a drug delivery device may include a housing having a distal end and a proximal end, a drug reservoir disposed in the housing and having a distal end and a proximal end, a drug delivery member in fluid communication with the distal end of the drug reservoir, a plunger disposed in and moveable relative to the drug reservoir, a carrier encasing the drug reservoir, and a plunger rod having a distal end and a proximal end. The plunger rod may be movable from (i) a first position, where the distal end of the plunger rod is spaced apart from the plunger to (ii) a second position, where the distal end of the plunger rod contacts the plunger. The drug delivery device may further include a drive mechanism that is coupled to the proximal end of the plunger rod and that is configured to move the plunger rod from the first position to the second position by a drive force $F_D$. The plunger rod, plunger, carrier, and drug reservoir may be movable from (i) the second position to (ii) a third position, where the carrier contacts the distal end of the housing. The drive mechanism may be configured to move the plunger rod, plunger, carrier, and drug reservoir from the second position to the third position. A ratio of total mass of the plunger rod, plunger, carrier, and drug reservoir $M_T$ to drive force $F_D$ of the drive mechanism ($M_T/F_D$) may be in a range of approximately a value greater than 0 kg/kgf to approximately 0.15 kg/kgf. In other embodiments, the ratio of the mass of the plunger rod, plunger, carrier, and drug reservoir to the drive force of the drive mechanism may be expanded beyond this range.

In accordance with a third exemplary aspect, a drug delivery device may include a housing having a distal end and a proximal end, a drug reservoir disposed in the housing and having a distal end and a proximal end, a drug delivery member in fluid communication with the distal end of the drug reservoir, a plunger disposed in and moveable relative to the drug reservoir, a carrier encasing the drug reservoir, and a plunger rod having a distal end and a proximal end. The plunger rod may be movable from (i) a first position, where the distal end of the plunger rod is spaced apart from the plunger to (ii) a second position, where the distal end of the plunger rod contacts the plunger. The drug delivery device may include a drive mechanism coupled to the proximal end of the plunger rod and is configured to move the plunger rod from the first position to the second position at a first velocity $\mu_1$. A mass of the plunger rod $M_P$ may be inversely proportional to a square of the first velocity $\mu_1$ of the plunger rod, wherein the plunger rod, plunger, carrier, and drug reservoir are movable from (i) the second position to (ii) a third position, where the carrier contacts the distal end of the housing. The drive mechanism may be configured to move the plunger rod, plunger, carrier, and drug reservoir from the second position to the third position at a second velocity $\mu_2$. A total mass of the plunger rod, plunger, carrier, and drug reservoir $M_T$ may be inversely proportional to a square of the second velocity $\mu_2$ of the plunger rod, plunger, carrier, and drug reservoir.

In accordance with a fourth exemplary aspect, a method of manufacturing a drug delivery device may include providing a reservoir, a plunger disposed in and moveable relative to the reservoir, and a drive mechanism where the drive mechanism is configured to move a plunger rod by a drive force $F_D$. Further, the method may include selecting a plunger rod having a mass $M_P$ based on a ratio of mass of the plunger rod to drive force ($M_P/F_D$) in a range of approximately a value greater than 0 kg/kgf to approximately 0.05 kg/kgf, providing the plunger rod having the mass based on the plunger rod mass to drive force ratio, and coupling the plunger rod to the drive mechanism.

In further accordance with any one or more of the foregoing first, second, third, or fourth aspects, a drug delivery device/method of manufacturing a drug delivery device may further include any one or more of the following forms. In a one form of the device, the drive force may be in a range of approximately 4.0 kgf to approximately 4.5 kgf and the mass of the plunger rod may be in a range of approximately 0.02 kg to approximately 0.2 kg.

In one form of the device, the drive force may be in a range of approximately 2.0 kgf to approximately 2.5 kgf and the mass of the plunger rod may be in a range of approximately 0.02 kg to 0.1 kg.

In one form of the device, the drive force may be in a range of approximately 4.0 kgf to approximately 4.5 kgf and the total mass of the plunger rod, plunger, carrier, and drug reservoir may be in a range of approximately 0.06 kg to approximately 0.6 kg.

In one form of the device, the drive force may be in a range of approximately 2.0 kgf to approximately 2.5 kgf and the total mass of the plunger rod, plunger, carrier, and drug reservoir may be in a range of 0.06 kg to approximately 0.3 kg.

In one form of the device, the reservoir may be a prefilled syringe.

In one form of the device, the mass of the plunger rod may be in a range of approximately 1.5 g to approximately 3 g.

In one form of the device, a mass of the carrier may be in a range of approximately 5 g to approximately 10 g and the mass of the plunger rod may be in a range of approximately 1.5 g to approximately 3 g.

In one form, the method may further include providing a housing having a distal end and a proximal end, selecting a carrier having a mass based on a ratio of total mass of the plunger rod, plunger, carrier, and reservoir to drive force ($M_T/F_D$) in a range of approximately a value greater than 0 kg/kgf to approximately 0.15 kg/kgf, providing the carrier having the mass based on the ratio of total mass of the plunger rod, plunger, carrier, and reservoir to drive force, and enclosing the reservoir with the carrier.

In one form of the method, providing the drive mechanism may include providing a spring configured to move the plunger rod at a drive force that is in a range of approximately 4.0 kgf to approximately 4.5 kgf and providing a plunger rod having a mass in a range of approximately 0.02 kg to approximately 0.2 kg.

In one form of the method, providing the drive mechanism may include providing a spring configured to move the plunger rod at a drive force that is in a range of approximately 2.0 kgf to approximately 2.5 kgf and providing a plunger rod having a mass in a range of approximately 0.02 kg to approximately 0.1 kg.

In one form of the method, providing the drive mechanism may include providing a spring configured to move the plunger rod at a drive force that is in a range of approximately 4.0 kgf to approximately 4.5 kgf and providing a plunger rod, plunger, carrier, and reservoir having a total mass in a range of approximately 0.06 kg to approximately 0.6 kg.

In one form of the method, providing the drive mechanism may include providing a spring configured to move the plunger rod at a drive force that is in a range of approximately 2.0 kgf to approximately 2.5 kgf and providing a plunger rod, plunger, carrier, and reservoir having a total mass in a range of approximately 0.06 kg to approximately 0.3 kg.

DETAILED DESCRIPTION

Figure 1:
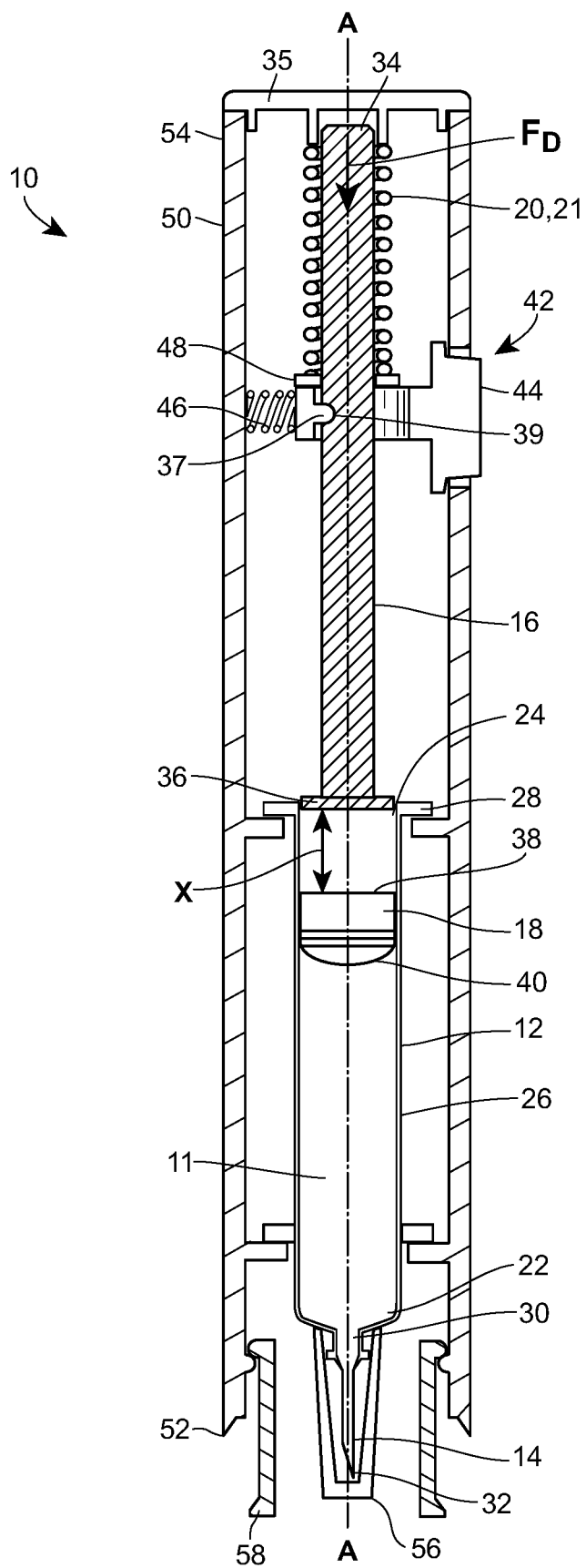
FIG. 1 illustrates a cross-sectional view of first exemplary drug delivery device in a preloaded configuration.
Figure 2:
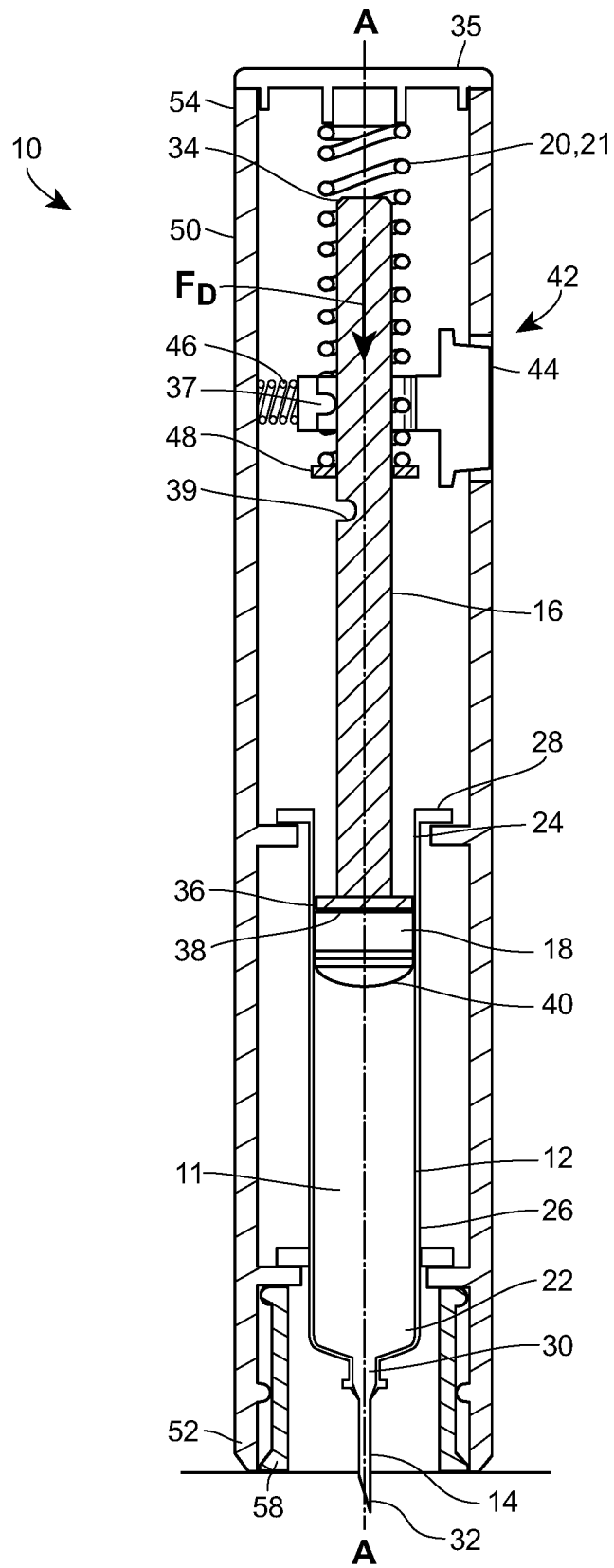
FIG. 2 illustrates a cross-sectional view of the drug delivery device of FIG. 1 at an impact event.
Figure 3:
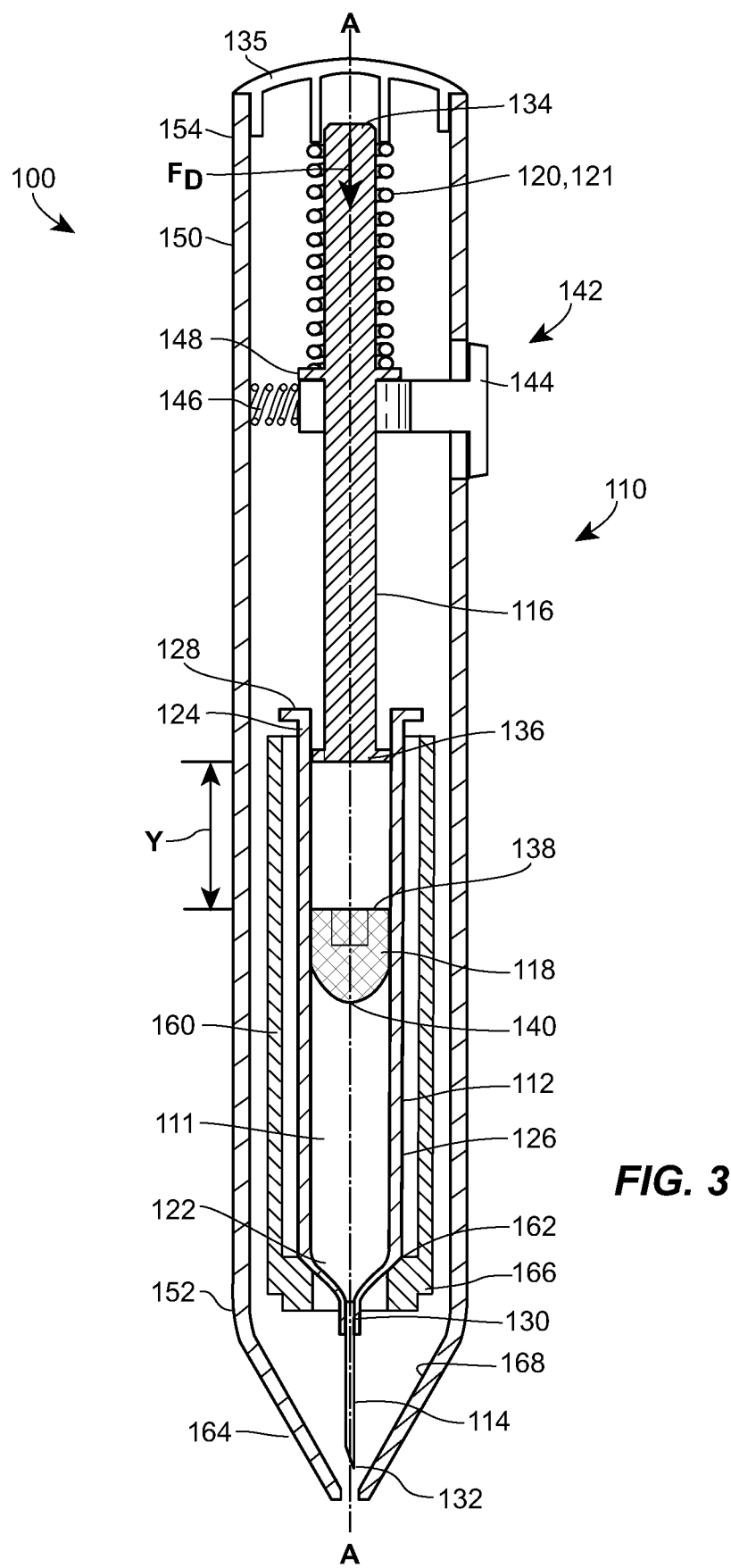
FIG. 3 illustrates a cross-sectional view of a second exemplary drug delivery device in a preloaded configuration.
Figure 4:
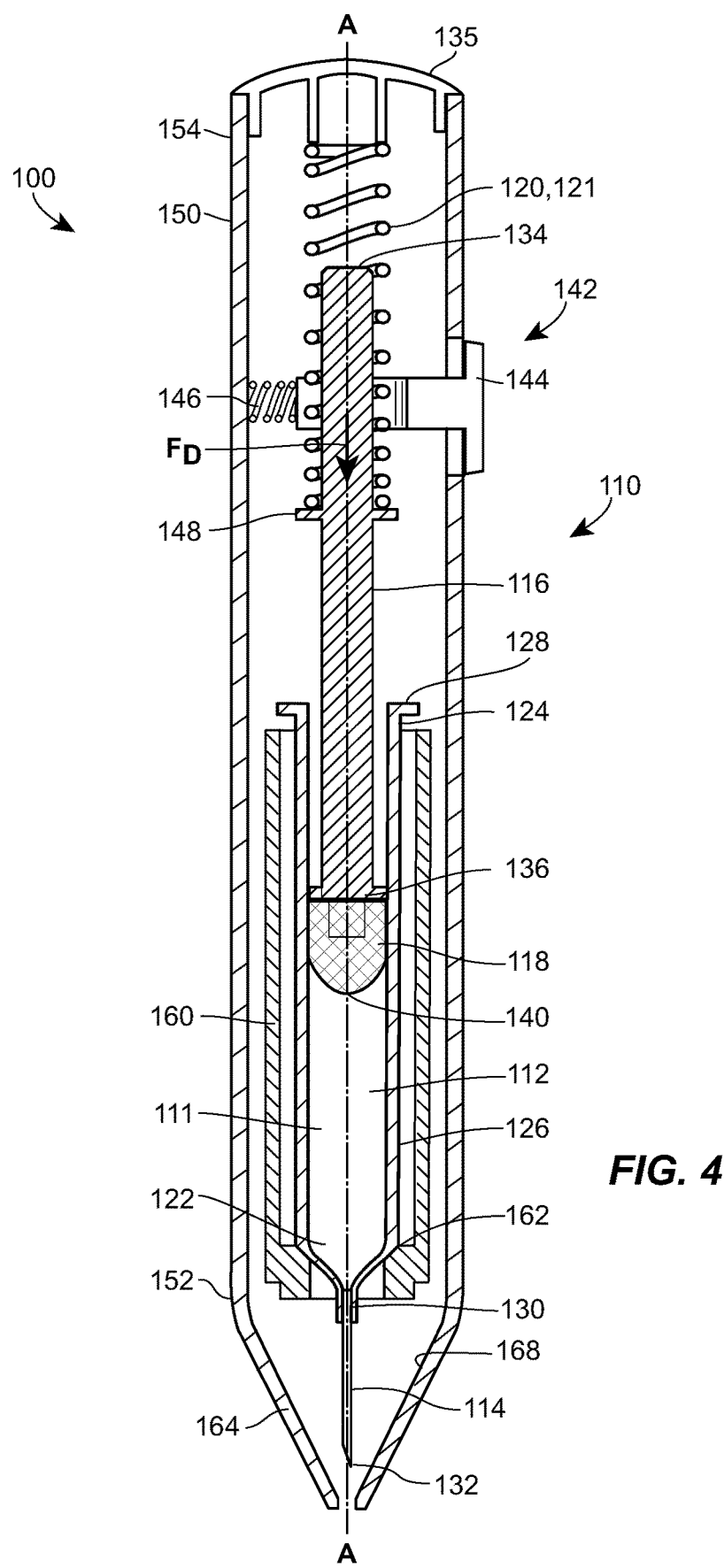
FIG. 4 illustrates a cross-sectional view of the drug delivery device of FIG. 3 at a first impact event.
Figure 5:
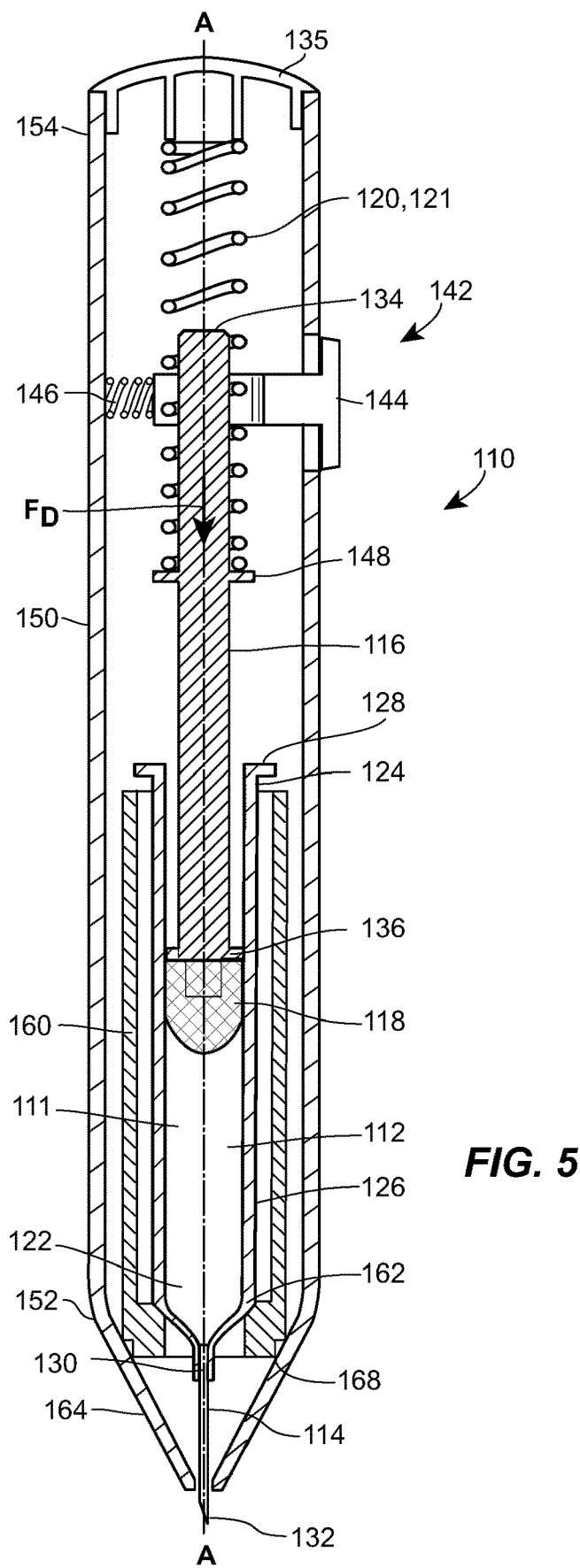
FIG. 5 illustrates a cross-sectional view of the drug delivery device of FIGS. 3 and 4 at a second impact event.
Figure 6:
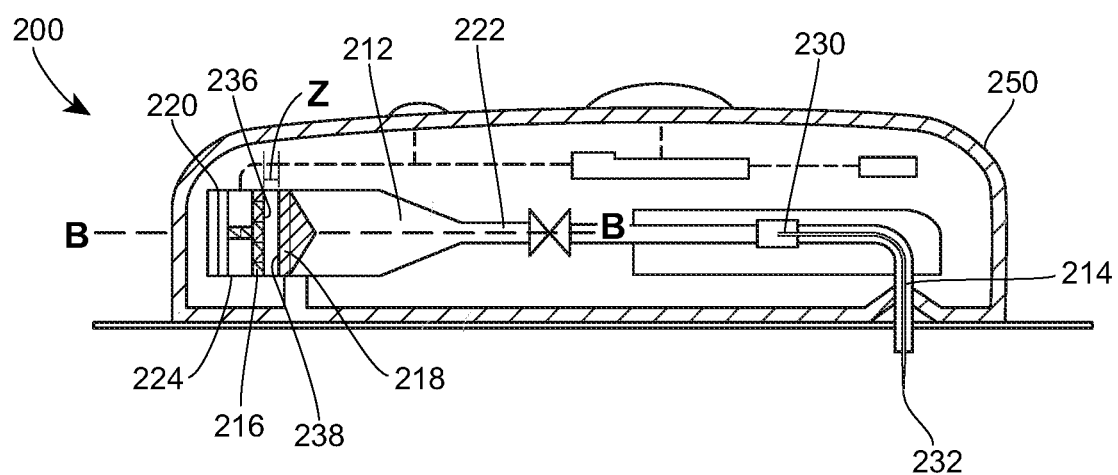
FIG. 6 illustrates a cross-sectional view of a third exemplary drug delivery device.

The drug delivery devices described and illustrated herein are designed to minimize component failure, and, specifically fracture of drug-filled reservoirs during injection. FIGS. 1-2 illustrate a first example of an autoinjector 10, which sustains one impact event; FIGS. 3-5 illustrate a second example of an autoinjector 100, which sustains two impact events; and FIG. 6 illustrates an example of an on-body injector 200, which sustains one impact event. The claimed subject matter may be applied to any force-driven drug delivery device that is susceptible to component failure caused by impact events, or any autoinjector with potential energy stored. As used herein, an "impact event" is used to describe the occurrence of a moving drug delivery device component, e.g. a plunger rod, contacting a stationary drug delivery device component, e.g., a plunger. As will be described further below, these impact events occur in existing drug delivery devices and may cause the drug delivery device to fail.

Turning first to FIG. 1, the autoinjector 10 includes a reservoir 12 configured to contain and/or containing a drug 11, a drug delivery member 14 configured to deliver the drug, a plunger rod 16 configured to drive a plunger 18, and a drive mechanism 20 configured to power drug delivery. The reservoir 12, which may be a prefilled syringe, an empty syringe, or other drug storage container, has a distal end 22 and a proximal end 24, where the drug delivery member 14 is in fluid communication with the distal end 22 of the reservoir 12. FIG. 1 illustrates the autoinjector 10 in a preloaded position where the plunger rod 16 is disposed at the proximal end 24 of the reservoir 12 and spaced way from the plunger 18, which is disposed within the reservoir 12 and is movable relative to the reservoir 12. The reservoir 12 in this example is a glass syringe and includes a thin-walled glass barrel 26 and an annular flange 28 located at the proximal end 24 of the reservoir 12.

The drug delivery member 14 is configured to deliver the stored drug to a patient. The drug delivery member 14 has a proximal end 30 in fluid communication with the distal end 22 of the reservoir 12, and a distal end 32 configured to be received within a patient. In FIGS. 1-2, the delivery member 14 is a needle, but other embodiments of a drug delivery device may include a hard or soft cannula or another component that facilitates fluid communication and delivery of a drug to the patient.

The drive mechanism 20 of this version includes a compressed coil spring 21 coupled to a proximal end 34 of the plunger rod 16. The drive mechanism 20 is configured to deliver an initial force of the drive mechanism 20, referred herein as the drive force $F_D$, to move the plunger rod 16 from the preloaded position, also referred herein as a first position where the plunger rod 16 is a distance X from the plunger 18, to a second position where a distal end 36 of the plunger rod 16 makes contact with a proximal end 38 of the plunger 18, as shown in FIG. 2. At the impact event shown in FIG. 2, the drive force $F_D$ initially causes the plunger rod 16 to impart an impact force on the plunger 18, before causing the plunger 18 to move linearly along a longitudinal axis A of the autoinjector 10, and through the reservoir 12. In this case, the longitudinal axis A coincides with a longitudinal axis of the reservoir 12. As the plunger 18 moves through the reservoir 12, a stopper located at the distal end 40 of the plunger 18 is configured to sealingly and slidably engage an inner wall of the glass barrel 26 to push the drug through the reservoir 12 and out through an open end of the drug delivery member 14. The term "drive force" may be a surrogate for the energy expended during the acceleration of the moving components, i.e. the plunger rod 16.

An actuator 42 oppositely located from the delivery member 14 is configured to activate the drive mechanism 20. In the example illustrated in FIGS. 1-2, the actuator 42 includes a button 44 and an actuator spring 46 and is configured to trigger the delivery of the drug to the patient by releasing the drive mechanism 20. In the preloaded position, the coil spring 21 of the drive mechanism 20 is compressed between an annular flange 48 of the plunger rod 16 and a rear cap 35 of the autoinjector 10. When the button 44 is pressed by the patient or a healthcare provider, the button 44 moves against the actuator spring 46 to release a lock tab 37 carried by the button 44 from a recess 39 in the plunger rod 14, and also releases the annular flange 48 of the plunger rod 16. As seen in FIG. 2, this releases the plunger rod 16 and allows the drive mechanism 20 to force the plunger rod 16 down relative to the orientation of FIGS. 1 and 2 and ultimately to contact and impact the plunger 18. Subsequent to the impact event shown in FIG. 2, the spring 20 biases the annular flange 48 in a distal direction, thereby moving the plunger rod 16 along the longitudinal axis A toward the distal end 22 of the reservoir 12. In another embodiment, the actuator 42 may be a soft switch that activates a motor that drives the plunger rod 16.

A patient may hold the drug delivery device 10 by a housing 50 which encloses the reservoir 12, drive mechanism 20, and plunger rod 16. The housing 50 is open at a distal end 52 and is closed at a proximal end 54. The housing 50 may be constructed as a single, unitary component or constructed from multiple components or sections that are combined into a single, integral unit. As illustrated in FIG. 1, the housing 50 may be attached to a needle shield 58 that is moveable relative to the distal end 32 of the delivery member 14. A removable sterile barrier 56 can also be disposed about the distal end 32 of the delivery member 14. The needle shield 58 may be biased in the distal direction by a biasing member (e.g., a spring), which is not shown.

To illustrate the impact event of the first example autoinjector 10, the method of operating the autoinjector 10 is described sequentially with reference to FIGS. 1-2. Prior to activating the actuator 42, the patient or healthcare provider may initially remove the removable sterile barrier 56, exposing the delivery member 14, and may press the needle shield 58 against the skin of the patient. The reaction force exerted by the patient's skin may push the needle shield 58 in and away from the distal end 32 of the drug delivery member 14 until the needle shield 58 reaches a position inside the housing 50, as shown in FIG. 2.

The patient or healthcare provider may then press the actuator button 44 of the actuator 42 to activate the drive mechanism 20, which drives the plunger rod 16 toward the plunger 18. As a result, the plunger rod 16 moves distance X from the first position shown in FIG. 1 to a second position shown in FIG. 2 where the distal end 36 of the plunger rod 16 initially impacts the proximal end 38 of the plunger 18. The drive mechanism 20 then drives the plunger 18 toward the distal end 22 of the syringe 12 to discharge the drug from the reservoir 12 and into the patient via the delivery member 14. The reservoir 12 remains stationary relative to the distal end 52 of the housing 50 as the plunger rod 16 and plunger 18 move through the reservoir 12. When delivery of the drug is complete, and/or when the plunger 18 has completed its delivery stroke, the patient or healthcare provider may remove the autoinjector 10 from the patient's skin.

Based on the requirements of the drug and the force generated by the drive mechanism 20 (i.e. a high viscosity drug requires a higher drive force to move the plunger through the reservoir), the plunger rod 16 may indirectly or directly impart an impact force onto the barrel 26 of the reservoir 12 when the plunger rod 16 impacts the plunger 18. If the plunger 18 is placed lower in the reservoir 12 such that the distance X increases, the impact becomes more important, i.e., more likely to be the cause of breakage. Here, plunger depth refers to a distance between a top of the flange 28 to the proximal end 38 of the plunger 18. Accordingly, "lower" refers to the plunger 18 being farther away from the flange 28 and closer to the delivery member 14. A load from the impact event generates pressure waves in the drug 11 that propagate through the glass barrel 26. For the combination of materials and geometries typical of glass syringes, a pressure wave will "couple" to the glass barrel 26 of the reservoir 12 as it propagates axially. This coupling results in a reduction of wave speed, and radial motion of the syringe. The coupled wave oscillates through the barrel 26 and may cause the barrel 26 to fracture.

To reduce pressure propagation throughout the glass barrel 26 with a given drive force $F_D$, the mass $M_P$ of the plunger rod 16 may be increased by a mass multiplier. More specifically, the mass $M_P$ of the plunger rod 16 may be increased based on a ratio $M_P/F_D$ of the mass $M_P$ of the plunger rod 16 to the drive force $F_D$ of the drive mechanism 20. The internal pressure of the reservoir 12 decreases when the ratio $M_P/F_D$ is in a range of approximately a value greater than 0 kg/kgf to approximately 0.05 kg/kgf. For example, if the drive force $F_D$ is in a range of approximately 4.0 kgf to approximately 4.5 kgf, then the mass $M_P$ of the plunger rod 16 may be in a range of approximately 0.02 kg to approximately 0.2 kg, and preferably between 0.06 kg to 0.2 kg. In another example, if the drive force $F_D$ is in a range of approximately 2.0 kgf to approximately 2.5 kgf, then the mass $M_P$ of the plunger rod 16 may be in a range of approximately 0.02 kg to approximately 0.1 kg, and preferably between 0.04 kg to 0.1 kg. The ranges in mass of the plunger rod 16 do not affect drug delivery time, i.e. the time from activation to completion. The principal intended to be captured is that the mass of the plunger rod $M_P$ and/or other moving components is maximized to mitigate the potential negative consequences of impact.

Impact force is also related to the velocity of the plunger rod 16 as it moves from the first position to the second position. To minimize the impact and instances of reservoir 12 fracture while maintaining delivery injection time, the plunger rod 16 of the drug delivery device 10 moves from the first position to the second position at a velocity $\mu_1$ that is approximately proportional to the inverse square root of the mass $M_P^{-1/2}$ of the plunger rod 16. According to this relationship, an increase in the mass $M_P$ of the plunger rod 16 reduces the velocity at which the plunger rod 16 travels through the reservoir 12, and therefore reduces force of impact imparted onto the plunger 18. A lower impact force at the first impact event minimizes risk of internal pressure build-up in the reservoir that causes component fracture. In a preferred example, the mass $M_P$ of the plunger rod 16 may be increased two to three times depending on the drive force $F_D$ of the drive mechanism 20. For example, if a conventional plunger rod is about 1.5 grams, then the mass may be increased to mass in a range of approximately 1.5 to 3 grams, and preferably between 2 and 3 grams.

Turning now to FIGS. 3-5, a second example autoinjector 100 includes a reservoir 112 configured to contain and/or contains a drug 111, a drug delivery member 114 configured to deliver the drug, a plunger rod 116 configured to drive a plunger 118, and a drive mechanism 120 configured to power drug delivery. The reservoir 112, which may be a prefilled syringe, an empty syringe, or other drug storage container, has a distal end 122 and a proximal end 124, where the drug delivery member 114 is in fluid communication with the distal end 122 of the reservoir 112. FIG. 3 illustrates the autoinjector 100 in a preloaded position where the plunger rod 116 is disposed at the proximal end 124 of the reservoir 112 and spaced way from the plunger 118, which is disposed within the reservoir 112 and is movable relative to the reservoir 112. The reservoir 112 in this example is a glass syringe and includes a thin-walled glass barrel 126, an annular flange 128 located at the proximal end 124, and a shoulder 162 disposed at the distal end 122 of the reservoir 112.

The drug delivery member 114 is configured to deliver the stored drug to a patient. The drug delivery member 114 has a proximal end 130 in fluid communication with the distal end 122 of the reservoir 112, and a distal end 132 configured to be received within a patient. In FIGS. 3-5, the delivery member 114 is a needle, but other embodiments of a drug delivery device may include a hard or soft cannula or another component that facilitates fluid communication and delivery of a drug to the patient.

An actuator 142 oppositely located from the delivery member 114 is configured to activate the drive mechanism 120. In the example illustrated in FIGS. 3-5, the actuator 142 includes a button 144 and an actuator spring 146 and is configured to trigger the delivery of the drug to the patient by releasing the drive mechanism 120 as described above and in relation to the previously illustrated autoinjector 10.

A patient may hold the drug delivery device 100 by a housing 150 which encloses the reservoir 112, drive mechanism 120, and plunger rod 116. The housing 150 is open at a distal end 52 and is closed at a proximal end 154 with a rear cap 135. The housing 150 may be constructed as a single, unitary component or constructed from multiple components or sections that are combined into a single, integral unit. The distal end 132 of the delivery member 114 is configured to extend beyond the distal end 152 of the housing 150 as illustrated in FIG. 5. A conical end 164 is located at the distal end 152 of the housing 150 and has a tapered shape. As will be discussed below, the tapered shape of the conical end 164 provides a stopping surface for the carrier 160 at the second impact event.

The drive mechanism 120 includes a compressed coil spring 121 coupled to a proximal end 134 of the plunger rod 116. The drive mechanism 120 is configured to deliver a drive force $F_D$ to move the plunger rod 116 from the preloaded position, also referred herein as a first position where the plunger rod 116 is a distance Y from the plunger 118, to a second position where a distal end 136 of the plunger 118 makes contact with a proximal end 138 of the plunger 118, as shown in FIG. 4. At the first impact event, the plunger rod 116 contacts the plunger 118 and initially imparts and impact force onto the plunger 118. The drive force $F_D$ then causes the plunger 118 to move the glass barrel 126 of the reservoir 112 linearly along a longitudinal axis A of the autoinjector 100. The frictional force between the plunger 118 and the glass barrel 126 causes the reservoir 112, along with the plunger rod 116 and plunger 118, to move in the distal direction. The shoulder 162 of the reservoir 112 is in contact with a distal end 166 of the carrier 160 and carries the carrier 160 from the second position illustrated in FIG. 4 to a third position illustrated in FIG. 5. The carrier 160 stops moving in the distal direction when the distal end 166 of the carrier 160 contacts an inner surface 168 of the conical end 164 of the housing 150. At this point, the momentum of the plunger rod 116 against the plunger 118 overcomes the frictional force between the plunger 118 and the glass barrel 126 and the plunger rod 116 and the plunger 118 are moveable through the reservoir 112 relative to the reservoir 112, carrier 160, and housing 150. The plunger 118 has a stopper at its distal end 140 and is configured to sealingly and slidably engage an inner wall of the reservoir 112 to discharge (e.g., eject) the drug from the reservoir 112 into the patient via the delivery member 114.

To illustrate the two impact events of the second example autoinjector 100, the method of operating the autoinjector 100 is described sequentially with reference to FIGS. 3-5. Initially, the patient or healthcare provider places the autoinjector 100 against the patient's skin, and presses the activation button 144 or otherwise initiates the actuator 142. The actuator 142 releases the compressed spring 121, which drives the plunger rod 116 from the first position illustrated in FIG. 3 to the second position illustrated in FIG. 4 where a distal end 136 of the plunger rod 116 impacts a proximal end 138 of the plunger 118. FIG. 4 illustrates the moment of the first impact event when the moving plunger rod 116 impacts the stationary plunger 118. After the first impact, the plunger rod 116 and plunger 118 advance both the reservoir 112 and the carrier 160 toward the conical end 164 of the housing 150. As illustrated in FIG. 5, the distal end 132 of the delivery member 114 extends through the open end of the housing 150 so that it may be inserted into the skin of the patient. Concurrently with the extension of the needle 114, the distal end 166 of the syringe carrier 160 contacts a point on the inside surface 168 of the conical end 164 of the housing 150, and remains in contact with the inside surface 168 while the plunger rod 116 and plunger 118 continue to advance in the distal direction to expel the drug into the patient.

Analysis of the autoinjector 100 using high-speed video has revealed that the two impact events impart significant impact forces to the reservoir 112. The first event occurs when the moving plunger rod 116 comes in contact with the stationary plunger 118 upon initial activation of the autoinjector 100. The load generates pressure waves that propagate through the fluid column. For the combination of materials and geometries typical of glass syringes, a pressure wave will "couple" to the glass barrel 126 as it propagates axially. This coupling results in a reduction of wave speed, and radial motion of the syringe 112. The second impact event occurs when the moving carrier 160 contacts the stationary conical end 164 of the housing 150. The forces of either or both of these two impacts can fracture the syringe barrel 126

To reduce pressure propagation throughout the glass barrel 126 with a given drive force $F_D$, the mass of the plunger rod $M_P$ may be increased by a mass multiplier as described above. Additionally, the mass of the carrier 160 may be increased based on a ratio $M_T/F_D$ of the total mass $M_T$ of an impact system 110, i.e. the plunger rod 116, plunger 118, reservoir 112, and carrier 160, to the drive force $F_D$ of the drive mechanism 120. The internal pressure of the reservoir 112 reaches a safe pressure value when the ratio $M_T/F_D$ of total mass $M_T$ to drive force $F_D$ is in a range of approximately a value greater than 0 kg/kgf to approximately 0.15 kg/kgf. For example, if the drive force $F_D$ is in a range of approximately 4.0 kgf to approximately 4.5 kgf, then the mass $M_T$ of the impact system 110 may be in a range of approximately 0.06 kg to approximately 0.6 kg, and preferably between 0.12 kg to 0.6 kg. In another example, if the drive force $F_D$ is in a range of approximately 2.0 kgf to approximately 2.5 kgf, then the mass $M_T$ of the impact system 110 may be in a range of approximately 0.06 kg to approximately 0.3 kg, and preferably between 0.12 kg to 0.3 kg. In other embodiments, the mass of the plunger 118, the mass of the reservoir 112, the mass of the carrier 160, the mass of the plunger rod 116, or any combination of all or one of the components of the impact system 110 may be increased so that the total combined mass $M_T$ of the impact system 110 to drive force $F_D$ ratio is within the desired range. As used herein, the term "impact system" refers to the components included in the second impact event, and according to the example illustrated in FIGS. 3-5, the "impact system" includes the plunger rod 116, the plunger 118, the reservoir 112, and the carrier 160. As used herein, the term "safe pressure value" refers to a range of internal pressure values of the autoinjector 100 that may be equal to or below peak pressure values.

Increase in impact force also relates to the velocity $\mu_1$ of the plunger rod 116 as it moves from the first position to the second position, and the velocity $\mu_2$ of the impact system 110 as it travels from the second position to the third position. To minimize the occurrences of fracture of the reservoir 112, the mass $M_P$ of a conventional plunger rod 116 may be increased to minimize the velocity $\mu_1$ of the plunger rod 116 when the plunger rod 116 impacts the plunger 118 at the first impact event, as described above. Additionally, the mass of the carrier 160 may be increased to reduce the velocity $\mu_2$ of the impact system 110 as the impact system 110 moves from the second position to the third position. In a preferred form, the total mass $M_T$ of the impact system 110 increases such that the velocity $\mu_2$ of the impact system 110 is proportional to the inverse square root of the mass $M_T^{-1/2}$ of the impact system 110. By reducing the velocity $\mu_2$, the force of impact imparted onto the conical end 164 of the housing 150 at the second impact event is reduced. The mass $M_T$ of the impact system 110 may be increased up to three times the mass of a conventional impact system, depending on the drive force $F_D$ of the drive mechanism 120.

While the drive mechanisms 20, 120 of the two autoinjectors 10, 100 thus far disclosed are described as including coil springs 21, 121, alternative versions of the drive mechanisms 20, 120 can include other force generating means including, for example, pressurized gas, chemical reaction devices, materials undergoing phase changes, etc. Moreover, other types of springs other than coil springs could be utilized if desired.

The improvements to conventional drug delivery devices disclosed herein may be applied to another drug delivery device, such as an on-body drug delivery device shown in FIG. 6. For example, a mass of a plunger rod 216 of an on-body injector 200 may be increased relative to the drive force $F_D$ of a drive mechanism 220 to avoid component failure. FIG. 6 illustrates a wearable on-body drug delivery device 200. The device 200 may include a housing 250 that can be attached to a patient. The drug delivery device 200 includes a reservoir 212, a drive 220, and a drug delivery member 214. The reservoir 212 may be defined at least in part by a rigid-walled cylinder 226 having a distal end 222 and a proximal end 224. A plunger 218 is disposed within the reservoir 212 and fitted to move along a longitudinal axis B of the reservoir 212 between the proximal end 224 and the distal end 222 to force a drug out of the reservoir 212 and into a drug delivery member 214. The drug delivery member 214 is in fluid communication with the reservoir 212 at a proximal end 230 of the drug delivery member 214.

The drive mechanism 220 may be similar in structure and operation to the drive mechanism 20, 120 for moving the plunger rod 16, 116 along the syringe 12, 112, as described above with reference to FIGS. 1-5. The drive mechanism 220, which may include a spring, is coupled to a proximal end 234 of a plunger rod 216. A distal end 236 of the plunger rod 216 is spaced a distance Z from a proximal end 238 of the plunger 218. In operation, the drive mechanism 220 drives the plunger rod 216 toward the plunger 218. The plunger rod 216 is configured to make contact with the proximal end 238 of the plunger 218 and to urge the plunger 218 along the B axis through the reservoir 212. Other drive mechanisms, such as pressurized gases, chemical reaction devices, materials undergoing phase changes and the like, may also be used to apply a drive force $F_D$ to the plunger rod 216 to move the plunger 218 along the cylinder 226.

A method of manufacturing a drug delivery device, e.g. drug delivery devices 10, 100, 200 illustrated in FIGS. 1-6 described herein, includes providing a reservoir, which may be a conventional syringe (see FIGS. 1-5) or a cylinder (see FIG. 6), a plunger disposed within and moveable relative to the reservoir, and a drive mechanism configured to move a plunger rod by a drive force $F_D$. To avoid component fracture, the method includes selecting a plunger rod having a mass $M_P$ based on a ratio $M_P/F_D$ of mass $M_P$ of the plunger rod to drive force $F_D$ in a range of approximately a value greater than 0 kg/kgf to approximately 0.05 kg/kgf. Once a suitable plunger rod has been manufactured or selected based on the desired mass, the plunger rod is provided and coupled to the drive mechanism. To manufacture a drug delivery device that sustains at least two impact events, a housing having a distal end and a proximal end may be provided. The method further includes selecting a carrier having a mass based on a ratio of total mass $M_T$ of the impact system, i.e. total combined mass of the plunger rod, plunger, reservoir, and carrier, to drive force $F_D$ ($M_T/F_D$) in a range of approximately a value greater than 0 kg/kgf to approximately 0.15 kg/kgf. Once a suitable carrier has been manufactured or selected based on the overall mass of the impact system 110, the carrier is provided to the device by enclosing the reservoir within the carrier.

Autoinjectors and on-body injectors provide sufficient drive power to facilitate delivery of viscous drugs at high injection speeds with little human effort. Just as each type of drug delivery device may be useful for a particular drug or patient, different types of drive mechanisms with varying power capabilities may be suitable for injecting particular types of drugs. To illustrate the method of the present disclosure, two types of drug delivery devices (a "one impact event device" and a "two impact event device") and two types of drive mechanisms may be chosen based on a particular drug.

To manufacture a drug delivery device that sustains one impact event without component failure, the method may include providing a spring that is configured to provide a drive force in a range of approximately 4.0 kgf to approximately 4.5 kgf. For this drive mechanism, a plunger rod having a mass in a range of approximately 0.02 kg to approximately 0.2 kg may be provided. In another example, the method may include providing a spring that is configured to provide a drive force in a range of approximately 2.0 kgf to approximately 2.5 kgf. For this drive mechanism, a plunger rod having a mass in a range of approximately 0.02 kg to approximately 0.1 kg may be provided.

To manufacture a drug delivery device that sustains at least two impact events without component failure, such as the autoinjector 100 in FIGS. 3-5, the method may include providing a spring that is configured to provide a drive force to the impact system, i.e. the plunger rod, the plunger, the carrier, and the reservoir, in a range of approximately 4.0 kgf to approximately 4.5 kgf. For this particular drive mechanism, an impact system may be provided that has a total mass in a range of approximately 0.06 kg to approximately 0.6 kg. If a drive force in the range of approximately 2.0 kgf to approximately 2.5 kgf is required, an impact system may be provided that has a total mass in a range of approximately 0.06 kg to approximately 0.3 kg. The drug delivery device according to the present disclosure is not limited to the drug delivery devices 10, 100, 200 illustrated in FIGS. 1-6, but may be any drug delivery device that is susceptible to component failure due to impact events.

The components of the drug delivery device, and specifically the plunger rod 16, 116, 216, plunger 18, 118, 218, reservoir 12, 112, 212, and carrier 160, may each be made from a material higher in density than materials conventionally used for these components. The drug delivery device may be made too meet the mass to drive force ratio of the present disclosure. Alternatively, existing drug delivery devices may be modified to meet the desired performance ratio by providing small weights or additives to the components or by replacing new components to existing devices. The components may be made of an AVF-type plastic, polymer, steel, and/or a combination of suitable materials.

The above description describes various systems and methods for use with a drug delivery device. It should be clear that the drug delivery device and method can further comprise use of a medicament listed below with the caveat that the following list should neither be considered to be all inclusive nor limiting. The medicament will be contained in a reservoir. In some instances, the reservoir is a primary container that is either filled or pre-filled for treatment with the medicament. The primary container can be a cartridge or a pre-filled syringe.

For example, the drug delivery device or more specifically the reservoir of the device may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgastrim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO:2 as set forth therein in FIG. 2 and/or the heavy chain of SEQ ID NO:4, as set forth therein in FIG. 4, each of which is individually and specifically incorporated by reference herein in its entirety fully as disclosed in the foregoing publication;

Myostatin binding proteins, peptibodies, and related proteins, and the like, including myostatin specific peptibodies, particularly those described in U.S. Publication No. 2004/0181033 and PCT Publication No. WO 2004/058988, which are incorporated by reference herein in their entirety particularly in parts pertinent to myostatin specific peptibodies, including but not limited to peptibodies of the mTN8-19 family, including those of SEQ ID NOS:305-351, including TN8-19-1 through TN8-19-40, TN8-19 con1 and TN8-19 con2; peptibodies of the mL2 family of SEQ ID NOS:357-383; the mL15 family of SEQ ID NOS:384-409; the mL17 family of SEQ ID NOS:410-438; the mL20 family of SEQ ID NOS:439-446; the mL21 family of SEQ ID NOS:447-452; the mL24 family of SEQ ID NOS:453-454; and those of SEQ ID NOS:615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publication No. 2004/097712, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned publication;

Ang2 specific antibodies, peptibodies, and related proteins, and the like, including but not limited to those described in PCT Publication No. WO 03/057134 and U.S. Publication No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2xL1(N); 2xL1(N) WT; Con4 (N), Con4 (N) 1K WT, 2xCon4 (N) 1K; L1C; L1C 1K; 2xL1C; Con4C; Con4C 1K; 2xCon4C 1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publication No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; AbIA1; AbIF; AbIK, AbIP; and AbIP, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in U.S. Publication No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing publication;

Also among non-limiting examples of anti-IGF-1R antibodies for use in the methods and compositions of the present invention are each and all of those described in:

(i) U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

(iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (ÿ4), deposited at the ATCC under number PTA-5214, and a light chain encoded by a polynucleotide in plasmid 15H12/19D12 LCF (ÿ4), deposited at the ATCC under number PTA-5220, as described therein; and (viii) U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, which are incorporated herein by reference in their entireties as to such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein), each of which is individually and specifically incorporated by reference herein in its entirety fully as disclosed in the foregoing publication;

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing publication and in Thakur et al. (1999), Mol. Immunol. 36:1107-1115. In addition, description of the properties of these antibodies provided in the foregoing publication is also incorporated by reference herein in its entirety. Specific antibodies include those having the heavy chain of SEQ ID NO:17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing publication. A specific antibody contemplated is antibody 1119 as disclosed in the foregoing U.S. publication and having a complete heavy chain of SEQ ID NO:17 as disclosed therein and having a complete light chain of SEQ ID NO:18 as disclosed therein;

TALL-1 specific antibodies, peptibodies, and the related proteins, and the like, and other TALL specific binding proteins, such as those described in U.S. Publication Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and OA-5d5 described in U.S. Pat. Nos. 5,686,292 and 6,468,529 and in PCT Publication No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in U.S. Publication No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publication No. WO 2006/081171, which is herein incorporated by reference in its entirety, particularly in parts pertinent to proteins that bind amyloid-beta proteins. One antibody contemplated is an antibody having a heavy chain variable region comprising SEQ ID NO:8 and a light chain variable region having SEQ ID NO:6 as disclosed in the foregoing publication;

c-Kit specific antibodies, peptibodies, related proteins, and the like, including but not limited to those described in U.S. Publication No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, which is incorporated herein by reference in its entirety, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-ÿ4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgastrim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFÿ monoclonal antibody); Reopro® (abciximab, anti-GP IIb/IIIa receptor monoclonal antibody); Actemra® (anti-IL6 Receptor mAb); Avastin® (bevacizumab), HuMax-CD4

(zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-ÿ4integrin mAb); Valortim® (MDX-1303, anti-*B. anthracis* protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Rÿ mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFÿ mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-ÿ5ÿ1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO029); anti-GM-CSF Receptor mAb (CAM-3001); anti-HepC mAb (HuMax HepC); anti-IFNÿ mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGÿ mAb (MDX-1307); anti-mesothelin dsFv-PE38 conjugate (CAT-5001); anti-PD1mAb (MDX-1106 (ONO-4538)); anti-PDGFRÿ antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab), as well as molecules, variants, analogs or derivatives thereof as disclosed in the following patents or patent applications, each of which is herein incorporated by reference in its entirety for all purposes: U.S. Pat. No. 8,030,547, U.S. Publication No. 2013/0064825, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223, 593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV12023; NV1034 and NV1042 (Vargehes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, bispecific T cell engager (BiTE®) antibodies, e.g. BLINCYTO® (blinatumomab), can be used in the device. Alternatively, included can be an APJ large molecule agonist e.g., apelin or analogues thereof in the device. Information relating to such molecules can be found in PCT Publication No. WO 2014/099984.

In certain embodiments, the medicament comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the medicament comprises a therapeutically effective amount of the anti-TSLP antibody designated as A5 within U.S. Pat. No. 7,982,016.

At least some of the techniques of this disclosure similarly can be applied to other drug delivery devices. For example, drug delivery devices generally suitable for simulation using the techniques of this disclosure can include hand-held injectors or on-body injectors. More generally, the techniques of this disclosure can be applied to devices in which a component that advances a liquid drug (or another liquid) uses coil compression, torsion, or another type of mechanical energy storage. Moreover, these techniques can be applied to non-mechanical systems such as propellant-driven systems.

Although the autoinjectors, on-body injector, systems, methods, and elements thereof, have been described in terms of exemplary embodiments, they are not limited thereto. The detailed description is to be construed as exemplary only and does not describe every possible embodiment of the invention because describing every possible embodiment would be impractical, if not impossible. Numerous alternative embodiments could be implemented, using either current technology or technology developed after the filing date of this patent that would still fall within the scope of the claims defining the invention.

It should be understood that the legal scope of the invention is defined by the words of the claims set forth at the end of this patent application. The appended claims should be construed broadly to include other variants and embodiments of same, which may be made by those skilled in the art without departing from the scope and range of equivalents of the on-body injector, autoinjectors, systems, methods, and their elements.

What is claimed is:

1. A drug delivery device comprising:
   a housing having a distal end and a proximal end;
   a reservoir disposed in the housing and having a distal end and a proximal end;
   a carrier encasing the reservoir;
   a drug delivery member in fluid communication with the distal end of the reservoir;
   a plunger disposed in and moveable relative to the reservoir;
   a plunger rod having a mass $M_P$, a distal end and a proximal end, the plunger rod being movable from (i) a first position, where the distal end of the plunger rod is spaced apart from the plunger to (ii) a second position, where the distal end of the plunger rod contacts the plunger; and
   a drive mechanism coupled to the proximal end of the plunger rod, the drive mechanism being configured to deliver a drive force $F_D$ to move the plunger rod from the first position to the second position,
   wherein a ratio of the mass of the plunger rod to the drive force of the drive mechanism ($M_P/F_D$) is in a range of approximately a value greater than 0 kg/kgf to approximately 0.05 kg/kgf;
   wherein the plunger rod, plunger, carrier, and reservoir have a total combined mass $M_T$; and
   wherein a ratio of the total combined mass $M_T$ of the plunger rod, plunger, carrier, and reservoir to the drive force $F_D$ of the drive mechanism ($M_T/F_D$) is in a range of approximately a value greater than 0 kg/kgf to approximately 0.15 kg/kgf.

2. The drug delivery device of claim 1, wherein the plunger rod, plunger, carrier, and reservoir are movable from (i) the second position to (ii) a third position, where the carrier contacts the distal end of the housing,
   the drive mechanism being configured to move the plunger rod, plunger, carrier, and reservoir from the second position to the third position.

3. The drug delivery device of claim 1, wherein the mass of the plunger rod is in a range of approximately 1.5 g to approximately 3 g and/or a mass of the carrier is in a range of approximately 5 g to approximately 10 g.

4. The drug delivery device of claim 1, wherein the drive force is in a range of approximately 4.0 kgf to approximately 4.5 kgf and the mass of the plunger rod is in a range of approximately 0.02 kg to approximately 0.2 kg.

5. The drug delivery device of claim 1, wherein the drive force is in a range of approximately 2.0 kgf to approximately 2.5 kgf and the mass of the plunger rod is in a range of approximately 0.02 kg to 0.1 kg.

6. The drug delivery device of claim 1, wherein the drive force is in a range of approximately 4.0 kgf to approximately 4.5 kgf and the total combined mass of the plunger rod, plunger, carrier, and reservoir is in a range of approximately 0.06 kg to approximately 0.6 kg.

7. The drug delivery device of claim 1, wherein the drive force is in a range of approximately 2.0 kgf to approximately 2.5 kgf and the total combined mass of the plunger rod, plunger, carrier, and reservoir is in a range of 0.06 kg to approximately 0.3 kg.

8. The drug delivery device of claim 1, wherein the reservoir is a prefilled syringe.

9. A method of manufacturing a drug delivery device, the method comprising:
   providing a reservoir, a plunger disposed in and moveable relative to the reservoir, a drive mechanism, and a drug delivery member in fluid communication with a distal end of the reservoir, wherein the drive mechanism is configured to move a plunger rod by a drive force $F_D$;
   providing a housing having a distal end and a proximal end, the reservoir disposed in the housing;
   enclosing the reservoir with a carrier;
   selecting the plunger rod having a distal end, a proximal end, and a mass $M_P$ based on a ratio of mass of the plunger rod to drive force ($M_P/F_D$) in a range of approximately a value greater than 0 kg/kgf to approximately 0.05 kg/kgf;
   providing the plunger rod having the mass based on the plunger rod mass to drive force ratio, wherein a ratio of total mass of the plunger rod, plunger, carrier, and reservoir to drive force ($M_T/F_D$) is in a range of approximately a value greater than 0 kg/kgf to approximately 0.15 kg/kgf; and;
   coupling the proximal end of the plunger rod to the drive mechanism, the drive mechanism arranged to deliver the drive force $F_D$ to move the plunger rod from (i) a first position, where the distal end of the plunger rod is spaced apart from the plunger to (ii) a second position, where the distal end of the plunger rod contacts the plunger.

10. The method of manufacturing the drug delivery device of claim 9, the method further comprising:
    selecting the carrier having a mass based on the ratio of total mass of the plunger rod, plunger, carrier, and reservoir to drive force ($M_T/F_D$); and
    providing the carrier having the mass based on the ratio of total mass of the plunger rod, plunger, carrier, and reservoir to drive force.

11. The method of manufacturing the drug delivery device of claim 9, wherein providing the drive mechanism includes providing a spring configured to move the plunger rod at a drive force that is in a range of approximately 4.0 kgf to approximately 4.5 kgf and providing the plunger rod having the mass $M_P$ in a range of approximately 0.02 kg to approximately 0.2 kg.

12. The method of manufacturing the drug delivery device of claim 9, wherein providing the drive mechanism includes providing a spring configured to move the plunger rod at a drive force that is in a range of approximately 2.0 kgf to approximately 2.5 kgf and providing the plunger rod having the mass $M_P$ in a range of approximately 0.02 kg to approximately 0.1 kg.

13. The method of manufacturing the drug delivery device of claim 9, wherein providing the drive mechanism includes providing a spring configured to move the plunger rod at a drive force that is in a range of approximately 4.0 kgf to approximately 4.5 kgf and providing the plunger rod, plunger, carrier, and reservoir having a total mass in a range of approximately 0.06 kg to approximately 0.6 kg.

14. The method of manufacturing the drug delivery device of claim 9, wherein providing the drive mechanism includes providing a spring configured to move the plunger rod at a drive force that is in a range of approximately 2.0 kgf to approximately 2.5 kgf and providing the plunger rod, plunger, carrier, and reservoir having a total mass in a range of approximately 0.06 kg to approximately 0.3 kg.

* * * * *

UNITED STATES PATENT AND TRADEMARK OFFICE
CERTIFICATE OF CORRECTION

PATENT NO. : 11,285,266 B2
APPLICATION NO. : 16/306810
DATED : March 29, 2022
INVENTOR(S) : Sean Fitzgibbon et al.

It is certified that error appears in the above-identified patent and that said Letters Patent is hereby corrected as shown below:

In the Claims

At Column 22, Line 31, "and;" should be -- and --.

Signed and Sealed this
Twenty-second Day of November, 2022

*Katherine Kelly Vidal*

Katherine Kelly Vidal
*Director of the United States Patent and Trademark Office*